(12) United States Patent
Miyanaga (10) Patent No.: US 11,717,250 B2
(45) Date of Patent: Aug. 8, 2023

(54) X-RAY CT DEVICE

(71) Applicant: SUMITOMO HEAVY INDUSTRIES, LTD., Tokyo (JP)

(72) Inventor: Hiroki Miyanaga, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 66 days.

(21) Appl. No.: 17/217,558

(22) Filed: Mar. 30, 2021

(65) Prior Publication Data

US 2021/0298710 A1    Sep. 30, 2021

(30) Foreign Application Priority Data

Mar. 31, 2020    (JP) .................................. 2020-062599

(51) Int. Cl.
| | |
|---|---|
| *A61B 6/00* | (2006.01) |
| *A61B 6/04* | (2006.01) |
| *A61B 6/06* | (2006.01) |
| *A61B 6/03* | (2006.01) |

(52) U.S. Cl.
CPC ............... *A61B 6/54* (2013.01); *A61B 6/032* (2013.01); *A61B 6/0407* (2013.01); *A61B 6/06* (2013.01); *A61B 6/4085* (2013.01); *A61B 6/4452* (2013.01); *A61B 6/5211* (2013.01)

(58) Field of Classification Search
CPC .............................. A61B 6/032; A61B 6/4452
See application file for complete search history.

(56) References Cited

U.S. PATENT DOCUMENTS

| | | | |
|---|---|---|---|
| 9,538,979 B2 | 1/2017 | Behling | |
| 9,898,662 B2 | 2/2018 | Tsuda et al. | |
| 10,124,191 B2 * | 11/2018 | Debatty | ................ A61B 6/032 |
| 2015/0036788 A1 | 2/2015 | Baba | |

FOREIGN PATENT DOCUMENTS

| | | |
|---|---|---|
| TW | 201503865 A | 2/2015 |
| TW | 201943435 A | 11/2019 |
| WO | WO-2014/041004 A1 | 3/2014 |
| WO | 2015032664 A1 | 3/2015 |

OTHER PUBLICATIONS

Office Action issued in Taiwanese Application No. 110111038, dated Nov. 7, 2022.
Office Action issued in Taiwanese Application No. 110111038, dated Oct. 14, 2021.

* cited by examiner

*Primary Examiner* — Dani Fox
(74) *Attorney, Agent, or Firm* — Michael Best & Friedrich LLP (57) ABSTRACT

An X-ray CT device includes: an X-ray source that irradiates an object to be imaged with an X-ray; an X-ray detector that is disposed on one side opposite to the X-ray source with a position, at which the object to be imaged is to be disposed, interposed therebetween and detects the X-ray having passed through the object to be imaged; and a rotary unit that supports the X-ray source and the X-ray detector and rotates the X-ray source and the X-ray detector together around the object to be imaged. A distance between the X-ray source and a predetermined reference position positioned in the object to be imaged is variable, and a distance between the reference position and the X-ray detector is variable.

13 Claims, 6 Drawing Sheets

X-RAY CT DEVICE

RELATED APPLICATIONS

The content of Japanese Patent Application No. 2020-062599, on the basis of which priority benefits are claimed in an accompanying application data sheet, is in its entirety incorporated herein by reference.

BACKGROUND

Technical Field

A certain embodiment of the present invention relates to an X-ray CT device.

Description of Related Art

In the related art, an X-ray CT device provided in a hadron therapy apparatus is known. This X-ray CT device includes an X-ray source and an X-ray detector provided in a rotary gantry, and the X-ray source and the X-ray detector are positioned with a patient, who is an object to be treated, interposed therebetween. The X-ray source and the X-ray detector are rotated around the patient with the rotation of the rotary gantry about the patient, so that the CT image data of the patient are obtained.

SUMMARY

According to an embodiment of the present invention, there is provided an X-ray CT device including: an X-ray source that irradiates an object to be imaged with an X-ray; an X-ray detector that is disposed on one side opposite to the X-ray source with a position, at which the object to be imaged is to be disposed, interposed therebetween and detects the X-ray having passed through the object to be imaged; and a rotary unit that supports the X-ray source and the X-ray detector and rotates the X-ray source and the X-ray detector together around the object to be imaged. A distance between the X-ray source and a predetermined reference position positioned in the object to be imaged is variable, and a distance between the reference position and the X-ray detector is variable.

DETAILED DESCRIPTION

In order to improve the quality of a CT image in the X-ray CT device, the irradiation dose of an X-ray needs to be increased. For this reason, there is a demerit that the exposure dose of a patient is increased. Alternatively, the quality of the CT image should be sacrificed in order to reduce the exposure dose of a patient. As described above, it is difficult to achieve both the improvement of the quality of a CT image and a reduction in the exposure dose of a patient in the CT device. It is desirable to provide an X-ray CT device that improves the quality of an image while suppressing an increase in the exposure dose of a patient.

The X-ray detector may include an X-ray detection surface that is perpendicular to a virtual straight line passing through the X-ray source and the reference position, and the X-ray detector may be capable of switching a state to a first state in which the virtual straight line passes through a center position of the X-ray detection surface and a second state in which the X-ray detection surface is displaced from the first state in a tangential direction of a rotation track and the virtual straight line passes through an end portion of the X-ray detection surface.

According to the invention, it is possible to provide an X-ray CT device that improves the quality of an image while suppressing an increase in the exposure dose of a patient.

Figure 1:
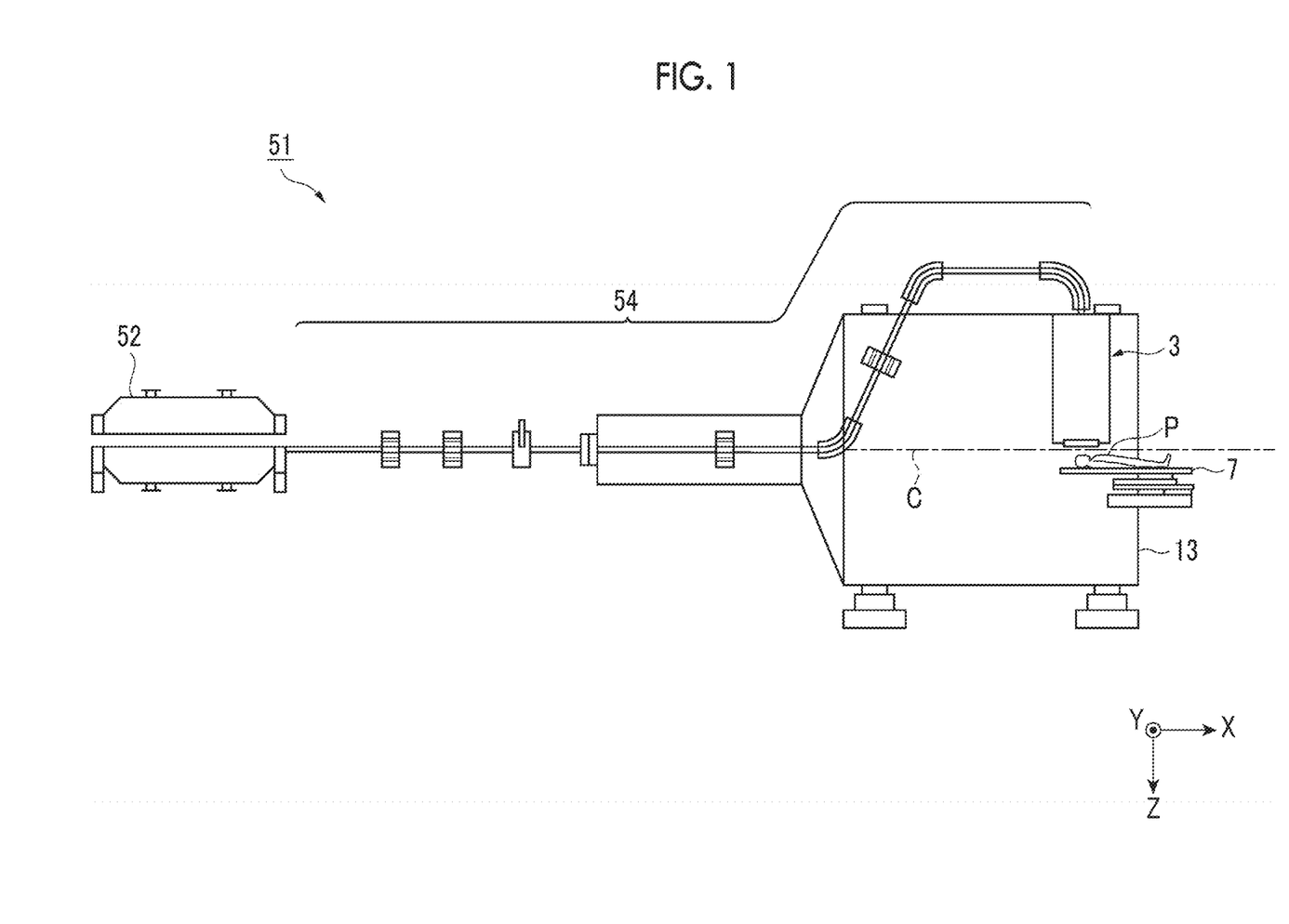
FIG. 1 is a diagram showing a proton therapy system that includes an X-ray CT device according to an embodiment.
Figure 2:
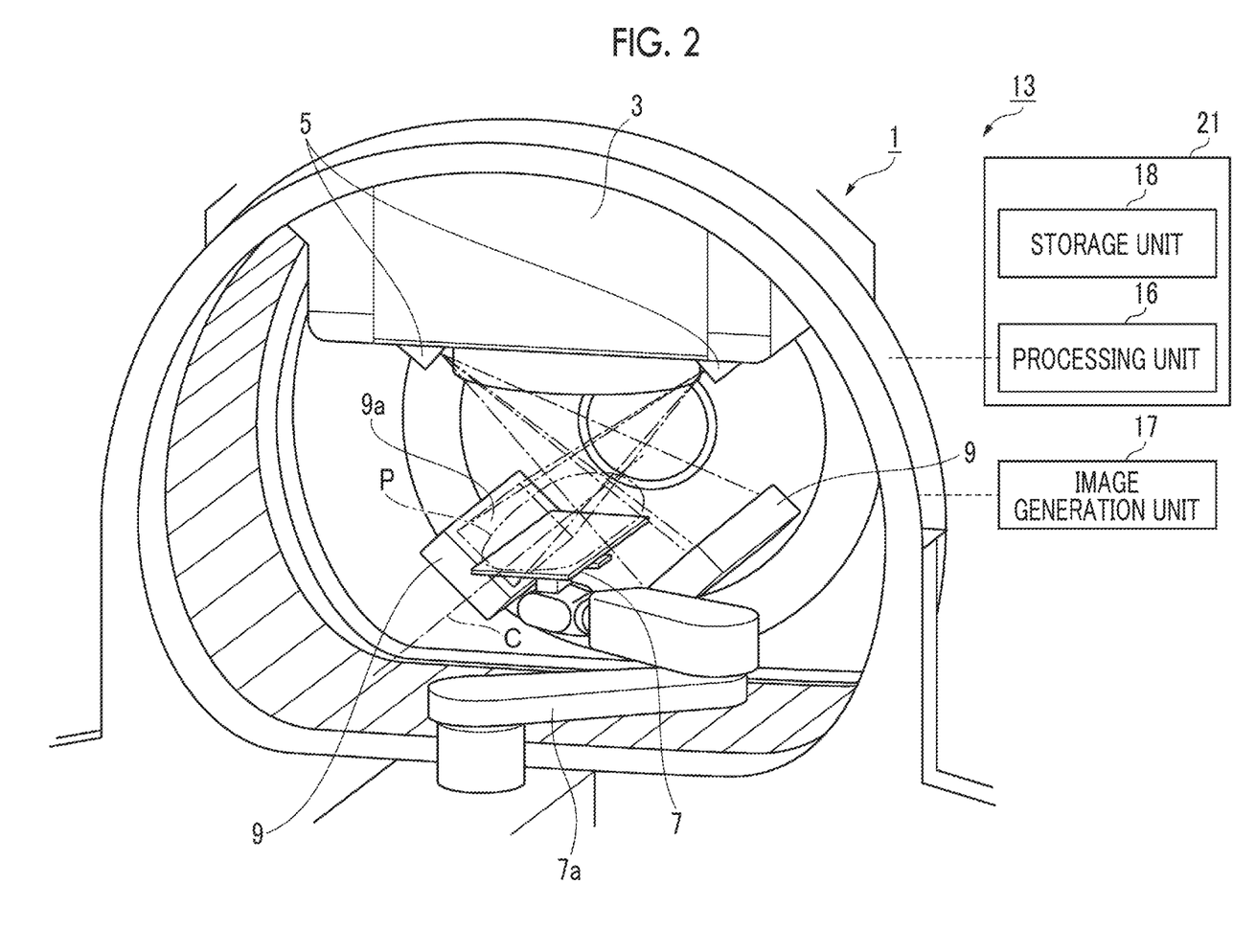
FIG. 2 is a perspective view showing a rotary gantry of the proton therapy system.

An X-ray CT device according to an embodiment of the invention will be described in detail below with reference to the drawings. As shown in FIGS. 1 and 2, the X-ray CT device 1 according to this embodiment is built in a proton therapy system 51 that is a kind of radiotherapy system. The proton therapy system 51 is, for example, an apparatus that irradiates a tumor in a patient P with a proton beam to treat the tumor. The proton therapy system 51 includes an accelerator 52 that accelerates charged particles to exit a charged particle beam, and an irradiator 3 that irradiates the patient P with a proton beam. Further, the proton therapy system 51 includes a rotary gantry 13 (rotary unit) that rotates the irradiator 3 around a treatment table 7 on which the patient P is to be placed, and a transport line 54 that connects the accelerator 52 to the irradiator 3 to transport the proton beam exited from the accelerator 52 up to the irradiator 3.

The X-ray CT device 1 is a type of CT device called a CBCT device (cone beam CT device), and is used to accurately align the patient P on the treatment table 7 of the proton therapy system 51. Specifically, prior to proton beam radiation therapy, the tomographic image (CT image) of the patient P set on the treatment table 7 is created using the X-ray CT device 1 and the position of the tumor or the like of the patient P (an object to be imaged) is recognized on the basis of this CT image. The CT image created by the X-ray CT device 1 is compared with the treatment planning CT image of the patient P created in advance by another CT device, so that the patient P is aligned on the treatment table 7. The alignment of the patient P on the treatment table 7 may be directly performed on the basis of the CT image created by the X-ray CT device 1.

The X-ray CT device 1 includes X-ray sources 5 that irradiate a patient P with X-rays, a treatment table 7 on which the patient P is to be placed, and X-ray detectors 9 that detect X-rays. The X-ray CT device 1 according to this embodiment includes two sets of the X-ray sources 5 and the X-ray detectors 9 as shown in FIG. 2, but may include one set of the X-ray source 5 and the X-ray detector 9. Further, the X-ray CT device 1 includes an image generation unit 17 that generates the CT image of the inside of the patient P on the basis of the X-rays detected by the X-ray detectors 9.

As shown in FIG. 2, the X-ray sources 5 and the X-ray detectors 9 are supported by the rotary gantry 13 and are adapted to be rotatable, and the X-ray sources 5 and the X-ray detectors 9 are rotated around an isocenter C as a single body. The isocenter C (reference position) is the origin of a coordinate that is used for CT image processing, processing for the treatment planning of proton therapy, and the like. The isocenter C is set to the center of rotation of the rotary gantry 13, and is also the center of rotation of the X-ray sources 5 and the X-ray detectors 9. However, since the rotation track of the rotary gantry 13 does not form a perfect circle, a mechanical isocenter, which is the center of gravity of the rotary gantry 13 positioned on the axis of rotation, serves as the isocenter C. Strictly speaking, the isocenter C determined in this way may not be an exact one point and may have a size having a width of about 1 mm. Separately, the center of gravity for the rotational drive of the rotary gantry 13, which is obtained from star-shot irradiation performed by the irradiator 3 for a proton beam or a Winston Lutz test, is called a radiation isocenter. This radiation isocenter is also not an exact one point and has a certain size, but the isocenter C is included in this radiation isocenter. Further, in a case where CT imaging is performed and a case where proton therapy is performed, the patient P is disposed so that the isocenter C is positioned inside the body (for example the position of the tumor) of the patient P.

Figure 3:
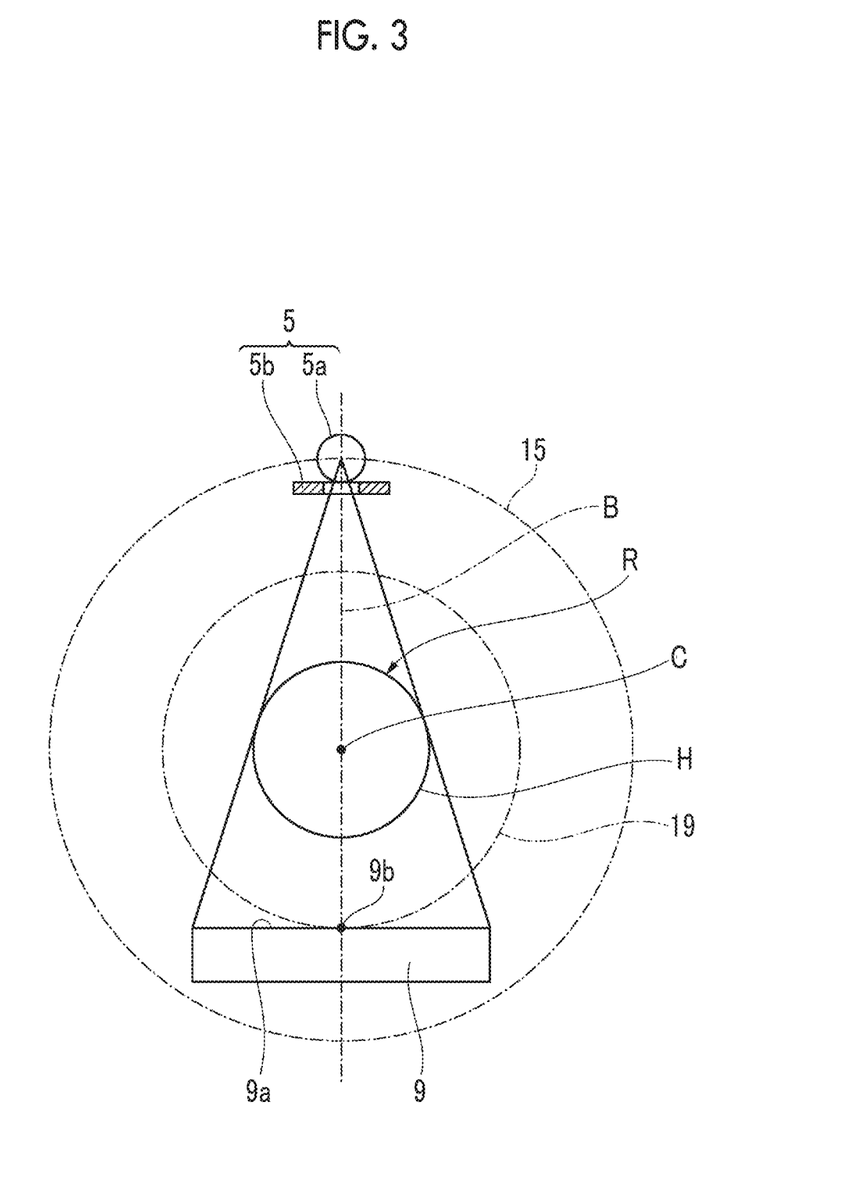
FIG. 3 is a diagram schematically showing a positional relationship between an X-ray source and an X-ray detector in a first state.

The X-ray source 5 includes an X-ray tube 5a and a collimator 5b (see FIG. 3). The X-ray tube 5a irradiates the treatment table 7 with a conical X-ray beam (cone beam) of which the vertex is positioned at the X-ray tube 5a. Further, the collimator 5b can adjust the spread angle of the X-ray beam of the X-ray tube 5a by opening and closing an opening thereof. The X-ray detector 9 is a flat panel detector (FPD), and includes an X-ray detection surface 9a that detects the X-ray emitted from the X-ray source 5.

The X-ray source 5 and the X-ray detector 9 are disposed in the rotary gantry 13 at positions opposite to each other with the treatment table 7 interposed therebetween. An X-ray having been emitted from the X-ray source 5 and having passed through the patient P placed on the treatment table 7 is detected by the X-ray detector 9, so that the X-ray image data of the patient P are acquired by the X-ray detector 9. In a case where the rotary gantry 13 is rotated by a predetermined angle (for example, about) 180° at this time, X-ray image data corresponding to each projection angle can be collected while a projection angle is changed. In this case, since the treatment table 7 on which the patient P is placed is supported by a support device 7a fixed to the floor of a building, the patient P is disposed near the isocenter C regardless of the rotation of the rotary gantry 13. Further, the image generation unit 17 performs image reconstruction processing, which uses predetermined calculation, on the basis of the X-ray image data collected by the X-ray detector 9, and generates the CT image of the inside of the patient P.

FIG. 3 is a diagram schematically showing the X-ray source 5 and the X-ray detector 9 along the line of sight parallel to the direction of the axis of rotation of the rotary gantry 13. One set of the X-ray source 5 and the X-ray detector 9 is shown in FIG. 3. However, since the other set thereof also has the same configuration as the set thereof shown in FIG. 3, repeated description and illustration thereof will be omitted. A circle 15 shown in FIG. 3 by a one-dot chain line is the rotation track of the X-ray source 5, and a circle 19 is the rotation track of the X-ray detection surface 9a. A virtual straight line B passing through the X-ray source 5 and the isocenter C passes through a center position 9b of the X-ray detection surface 9a and is perpendicular to the X-ray detection surface 9a. The passing range of the X-ray, which is exited from the X-ray source 5 and is detected by the X-ray detection surface 9a, is represented by a triangle of which the vertices are positioned at the X-ray source 5 and both ends of the X-ray detection surface 9a. Further, in a case where the passing range is rotated about the isocenter C, a region where all the rotated passing ranges overlap is represented by a region inside a circle H inscribed in all the rotated triangles. Such a region R may also be called a visualization region, a field of view (FOV), or the like. In a case where CT imaging is performed, the cross section of the patient P needs to be included in the FOV.

Figure 4:
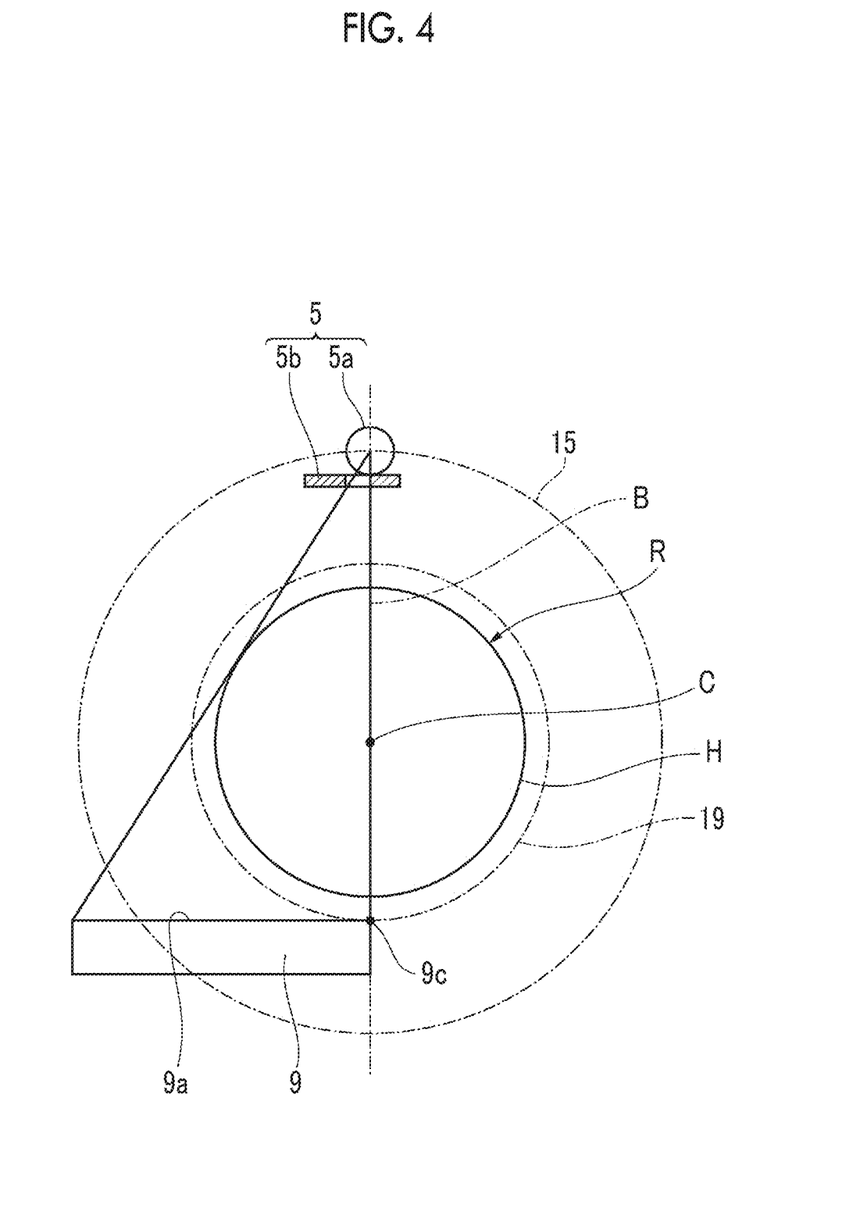
FIG. 4 is a diagram schematically showing a positional relationship between the X-ray source and the X-ray detector in a second state.

Further, CT imaging can also be performed in a state where the installation position of the X-ray detector 9 is changed in the X-ray CT device 1 to set the X-ray source 5 and the X-ray detector 9 to a state shown in FIG. 4. In the state shown in FIG. 4, the X-ray detection surface 9a is displaced in the tangential direction of the rotation track (circle 19) and the virtual straight line B passing through the X-ray source 5 and the isocenter C passes through an end portion 9c of the X-ray detection surface 9a. Since FOV (region R) in this state is larger than that in a state shown in FIG. 3 as geometrically understood, it is possible to cope with even CT imaging of a patient P having a large waist circumference. Hereinafter, the state shown in FIG. 3 will be referred to as "first state" and the state shown in FIG. 4 will be referred to as "second state".

Further, a distance between the isocenter C and the X-ray source 5 is variable in the X-ray CT device 1. That is, since the position of the X-ray source 5 can be moved in a rotational radial direction (the direction of the virtual straight line B) in the rotary gantry 13, the radius of rotation of the X-ray source 5 (the radius of the circle 15) can be changed. Likewise, a distance between the isocenter C and the X-ray detector 9 is variable in the X-ray CT device 1. That is, since the position of the X-ray detector 9 can be moved in the rotational radial direction (the direction of the virtual straight line B) in the rotary gantry 13, the radius of rotation of the X-ray detector 9 (the radius of the circle 19) can be changed. For example, various publicly known mechanisms, such as a mechanism for sliding the X-ray source 5 or the like in the direction of the virtual straight line B, can be employed to make the position of each of the X-ray source 5 and the X-ray detector 9 variable in the rotary gantry 13.

Settings for CT imaging to be performed by the above-mentioned X-ray CT device 1 will be described with reference to a flowchart shown in FIG. 5 and schematic diagrams shown in FIGS. 6A to 6D.

The X-ray CT device 1 includes a processing unit 16 (see FIG. 2) that collectively controls the operations of the X-ray sources 5 and the X-ray detectors 9, and the processing unit 16 is, for example, one component of the computer 21 (see FIG. 2). The computer 21 includes a storage unit 18 (see FIG. 2) that stores information, and a predetermined computer program represented by the flowchart shown in FIG. 5 is stored in the storage unit 18. Settings to be described below may be automatically performed by the processing unit 16. In this case, the processing unit 16 can move the support position of each X-ray source 5 with respect to the rotary gantry 13 in the rotational radial direction of the rotary gantry 13 to set the position of each X-ray source 5. Further, the processing unit 16 can move the support position of each X-ray detector 9 with respect to the rotary gantry 13 in the rotational radial direction of the rotary gantry 13 and in the tangential direction of the rotation track of the rotary gantry 13 to set the position of each X-ray detector 9. In order to enable the position setting to be performed, the rotary gantry 13 may be provided with driving units (not shown) that move the X-ray sources 5 and the X-ray detectors 9 under the control of the processing unit 16, respectively, and sensors (not shown) that detect the respective positions of the X-ray sources 5 and the X-ray detectors 9 and transmit the detected positions to the processing unit 16. Further, in a case where the computer program is executed by the computer 21, settings to be described below may be performed in cooperation with the driving units, the sensors, and the like that are controlled by the processing unit 16.

Figure 5:
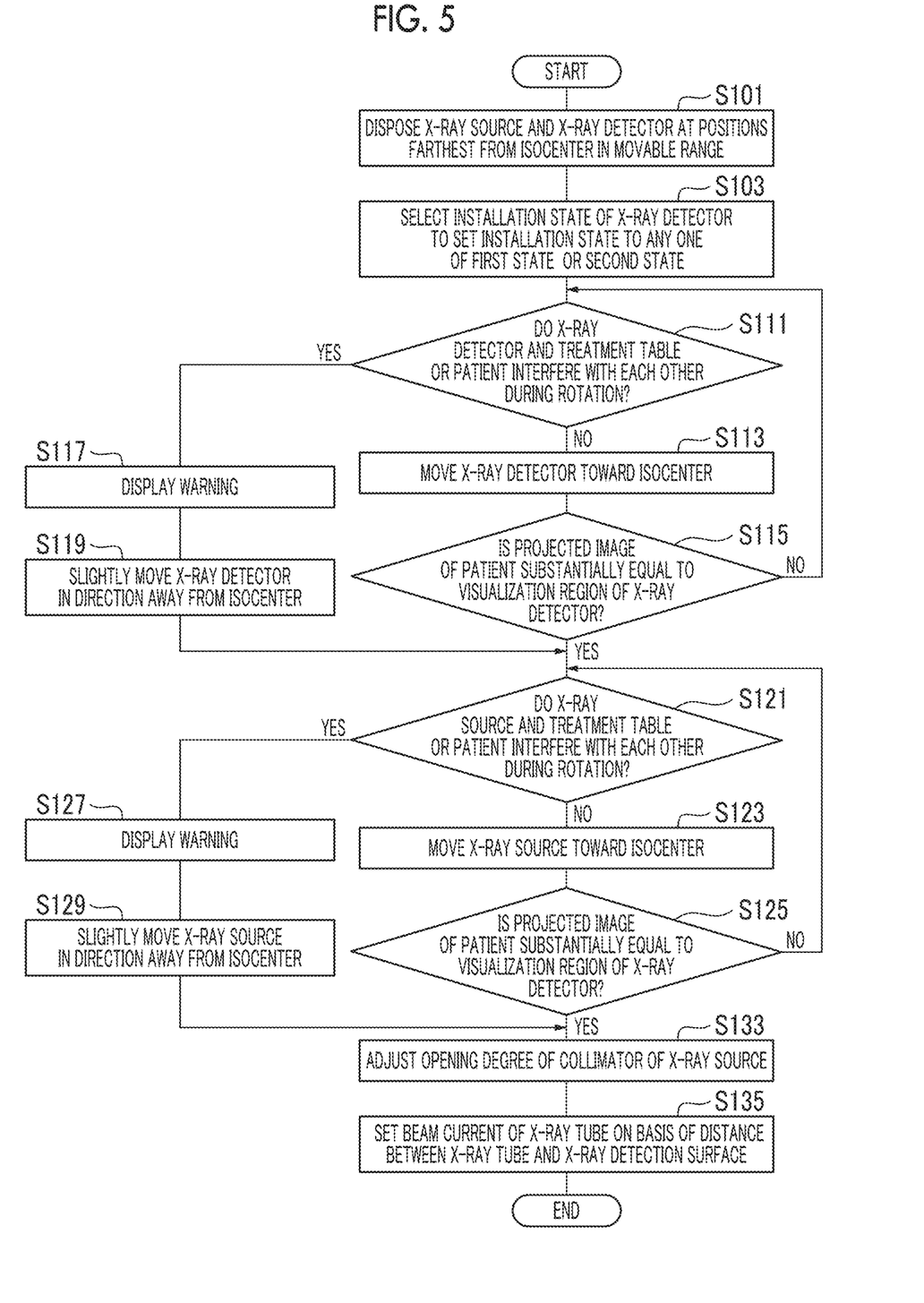
FIG. 5 is a flowchart showing the settings of the X-ray CT device.
Figure 6A:
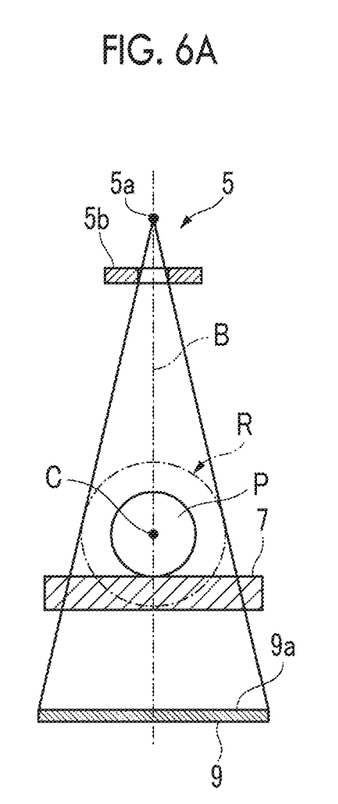
FIGS. 6A to 6D are diagrams sequentially showing the settings of the X-ray CT device.

In the settings, first, the X-ray source 5 and the X-ray detector 9 are disposed at positions farthest from the isocenter C in a movable range as shown in FIG. 6A (S101 in FIG. 5). In this case, the opening degree of the collimator 5b of the X-ray source 5 is adjusted so that the full width of the X-ray detection surface 9a is irradiated with an X-ray. Subsequently, one of a first state (FIG. 3) and a second state (FIG. 4) to which the installation state of the X-ray detector 9 is to be set is selected on the basis of the size of the patient P, or the like, and the X-ray detector 9 is installed in the rotary gantry 13 in the selected any one installation state (S103 in FIG. 5). Here, the size of the patient P may be measured on the basis of an optical sensor and a distance sensor. Alternatively, the size of the patient P may be recognized on the basis of information obtained from treatment planning CT. In a case where the size of the patient P is smaller than a prescribed size, the first state is selected. In a case where the size of the patient P is larger than the prescribed size, the second state is selected. A case where the first state is selected will be used as an example to describe subsequent processing below. However, since processing in a case where the second state is selected is also the same as that in a case where the first state is selected, repeated description will be omitted.

Figure 6B:
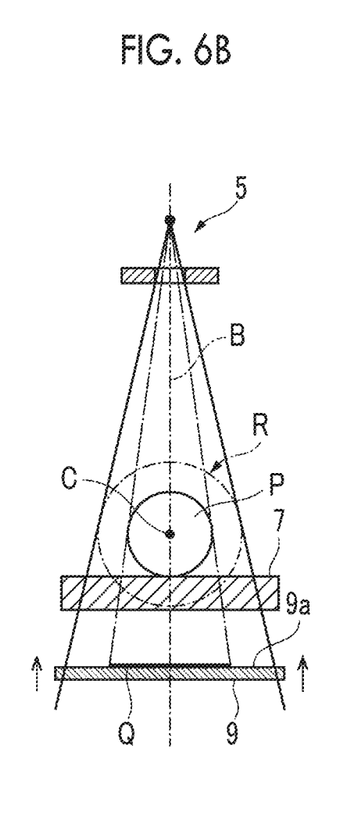

Subsequently, as shown in FIG. 6B, the X-ray detector 9 is moved so as to approach the isocenter C and is installed (S113 in FIG. 5). Here, in a case where a distance between the X-ray detector 9 and the isocenter C is too short, there is a possibility that the X-ray detector 9 and the treatment table 7 or the patient P may interfere with each other during the rotation of the rotary gantry 13. Accordingly, the X-ray detector 9 is installed at a position as close as possible to the isocenter C in a range where such interference does not occur. Further, here, the X-ray detector 9 is installed so that the width of a projected image Q of the patient P projected onto the X-ray detector 9 from the X-ray source 5 and the width of the visualization region (X-ray detection surface 9a) of the X-ray detector 9 are as close as possible to each other. That is, the X-ray detector 9 is installed so that the visualization region of the X-ray detector 9 as wider as possible can be used.

Specifically, processing of S111 to S119 shown in FIG. 5 is performed as described below as the position setting of the X-ray detector 9. First, the 3D models of the X-ray detector 9, the X-ray source 5, the treatment table 7, and the patient P are created and stored in the processing unit 16 in advance. The 3D model of the patient P is calculated from body surface information of the patient P, and the body surface information is obtained from planning CT in a case where treatment planning for the patient P is created. In S111, a simulation based on the current position information of the X-ray detector 9 and the X-ray source 5 and the 3D models is performed and it is determined whether or not interference between the X-ray detector 9 and the treatment table 7 or the patient P occurs during the rotation of the rotary gantry 13 (S111 in FIG. 5).

In a case where it is determined in S111 that interference occurs, a screen warning an operator is displayed on an information output unit (information display screen) (not shown) connected to the processing unit 16 (S117 in FIG. 5). Further, the X-ray detector 9 is slightly moved in a direction away from the isocenter C (S119 in FIG. 5), so that the X-ray detector 9 is installed at a position where the interference does not occur. After that, processing proceeds to S121 to be described later. In this case, the current position of the X-ray detector 9 is set as the limit position (a limit position close to the isocenter C) of the movement range of the X-ray detector 9, and the movement of the X-ray detector 9 toward the isocenter C from the limit position may be inhibited.

On the other hand, in a case where it is determined in S111 that interference does not occur, the X-ray detector 9 is moved by a predetermined distance so as to approach the isocenter C and is installed (S113 in FIG. 5). After that, it is determined whether or not the width of the projected image Q of the patient P and the width of the visualization region (X-ray detection surface 9a) of the X-ray detector 9 are substantially equal to each other (S115 in FIG. 5). That is, it is determined whether or not a difference between the width of the projected image Q of the patient P and the width of the visualization region is equal to or smaller than a predetermined length. In a case where it is determined in S115 that the width of the projected image Q and the width of the visualization region of the X-ray detector 9 are substantially equal to each other, processing proceeds to S121 to be described later. In other cases, the processing is repeated again from S111 having been described above.

The projected image Q in S115 is acquired as a virtual projected image (DRR: Digitally Reconstructed Radiographs) in the processing unit 16 in advance on the basis of planning CT in a case where treatment planning for the patient P is created. Then, in S115, DDR is obtained from the current position information of the X-ray detector 9 and the X-ray source 5 and the projected image Q of the patient P is obtained by a simulation.

Figure 6C:
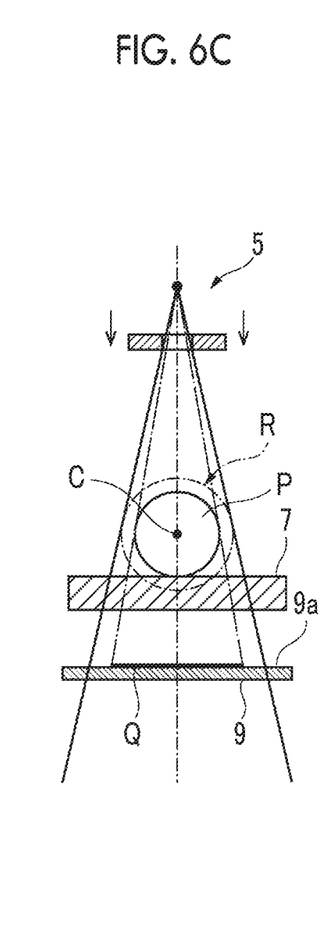

Subsequently, as shown in FIG. 6C, the X-ray source 5 is moved so as to approach the isocenter C and is installed (S123 in FIG. 5). Here, in a case where a distance between the X-ray source 5 and the isocenter C is too short, there is a possibility that the X-ray source 5 and the treatment table 7 or the patient P may interfere with each other during the rotation of the rotary gantry 13. Accordingly, the X-ray source 5 is installed at a position as close as possible to the isocenter C in a range where such interference does not occur. Further, here, the X-ray source 5 is installed so that the width of the projected image Q of the patient P projected onto the X-ray detector 9 from the X-ray source 5 and the width of the visualization region (X-ray detection surface 9a) of the X-ray detector 9 are as close as possible to each other. That is, the X-ray source 5 is installed so that the visualization region of the X-ray detector 9 as wider as possible can be used.

Specifically, processing of S121 to S129 shown in FIG. 5 is performed as the position setting of the X-ray source 5. Since processing for the position setting of the X-ray source 5 performed by S121 to S129 is the same as processing for the position setting of the X-ray detector 9 performed by S111 to S119 having been described above, repeated description will be omitted.

Figure 6D:
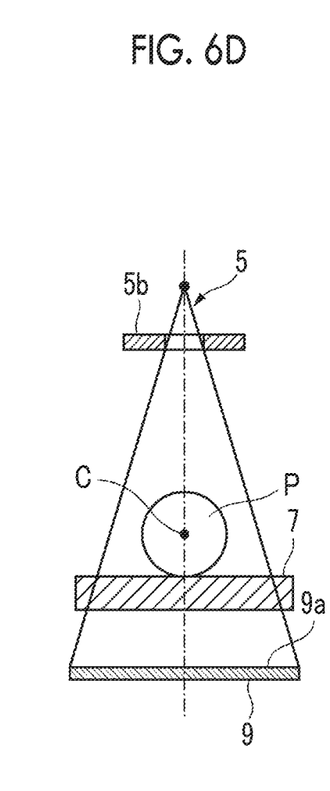

Subsequently, the opening degree of the collimator 5b of the X-ray source 5 is adjusted again, so that an irradiation field is adjusted to a range optimal for the active area (X-ray detection surface 9a) of the X-ray detector 9 as shown in FIG. 6D (S133 in FIG. 5). Here, the opening degree of the collimator 5b to be adjusted may be obtained using the above-mentioned simulation of DDR. For example, here, the full width of the X-ray detection surface 9a is irradiated with an X-ray. Here, the opening degree of the collimator 5b may be intentionally reduced so that an irradiation field irradiated by the X-ray source 5 is adjusted to the range of the region of interest of a target (patient P). In this case, since the irradiation field is narrowed and scattered rays are reduced, the quality of a CT image is improved. Next, the beam current (exposure parameter) of the X-ray tube 5a is set on a basis of a distance between the X-ray tube 5a and the X-ray detection surface 9a so that an X-ray dose required for obtaining the sufficient quality of a CT image is obtained (S135 in FIG. 5).

In the above-mentioned X-ray CT device 1, the width of the projected image Q of the patient P and the width of the visualization region of the X-ray detector 9 can be as close as possible to each other and a distance between the X-ray source 5 and the X-ray detection surface 9a can be made as short as possible in a range where the X-ray source 5 and the X-ray detector 9 do not interfere with other devices (the treatment table 7 and the like) during rotating. Accordingly, since a distance between the X-ray source 5 and the X-ray detection surface 9a is reduced, the quality of a CT image to be obtained from CT imaging is improved without an increase in an X-ray dose. Further, a reduction in scattered rays caused by a reduction in a distance between the X-ray source 5 and the X-ray detection surface 9a also contributes to the improvement of the quality of a CT image. Accordingly, according to this X-ray CT device 1, it is possible to improve the quality of an image while suppressing an increase in the X-ray exposure dose of the patient P by suppressing an increase in an X-ray dose.

Further, not only the first state (FIG. 3) but also the second state (FIG. 4) can be selected for imaging in the X-ray CT device 1. Accordingly, since FOV can be increased by the second state according to the waist circumference of a patient P, or the like, it is easy to deal with even a patient P having a large waist circumference.

The invention can be embodied in various forms including various modifications and improvements on the basis of based on the knowledge of those skilled in the art in addition to the above-mentioned embodiment. Further, it is also possible to form a modification example using the technical matters described in the above-mentioned embodiment. The components of the respective embodiments may be appropriately used in combination.

In the embodiment, the position setting of the X-ray source 5 (S121 to S129 in FIG. 5) has been performed after the position setting of the X-ray detector 9 (S111 to S119 in FIG. 5). However, this order may be changed so that the position setting of the X-ray detector 9 (S111 to S119 in FIG. 5) may be performed after the position setting of the X-ray source 5 (S121 to S129 in FIG. 5). Further, at least a part of the processing of the flowchart shown in FIG. 5 may be manually performed by the operator of the X-ray CT device 1. Furthermore, one example where the X-ray CT device according to the invention is applied to a CBCT device built in a proton therapy system has been described in the embodiment, but the invention can also be applied to a surgical X-ray CT device or a dental X-ray CT device.

It should be understood that the invention is not limited to the above-described embodiment, but may be modified into various forms on the basis of the spirit of the invention. Additionally, the modifications are included in the scope of the invention.

What is claimed is:

1. An X-ray CT device comprising:
   an X-ray source that irradiates an object to be imaged with an X-ray;
   an X-ray detector that is disposed on one side opposite to the X-ray source with a position, at which the object to be imaged is to be disposed, interposed therebetween and detects the X-ray having passed through the object to be imaged; and
   a rotary unit that supports the X-ray source and the X-ray detector and rotates the X-ray source and the X-ray detector together around the object to be imaged,
   wherein a distance between the X-ray source and a predetermined reference position positioned in the object to be imaged is variable in a rotational radial direction of the rotary unit,
   a distance between the reference position and the X-ray detector is variable in the rotational radial direction of the rotary unit, and
   the X-ray source and the X-ray detector are configured to move in the rotational radial direction of the rotary unit.

2. The X-ray CT device according to claim 1,
   wherein the X-ray source includes an X-ray tube and a collimator.

3. The X-ray CT device according to claim 2,
   wherein the X-ray tube irradiates the object to be imaged with a substantially conical X-ray beam of which a vertex is positioned at the X-ray tube, and
   the collimator includes an opening and adjusts a spread angle of the X-ray beam of the X-ray tube by opening and closing the opening.

4. The X-ray CT device according to claim 1, further comprising:
   an image generation unit that generates a CT image on the basis of the X-ray detected by the X-ray detector.

5. The X-ray CT device according to claim 1, further comprising:
   a processing unit that collectively controls operations of the X-ray source and the X-ray detector.

6. The X-ray CT device according to claim 5,
   wherein the processing unit moves a support position of the X-ray source with respect to the rotary unit in the rotational radial direction of the rotary unit to set a position of the X-ray source.

7. The X-ray CT device according to claim 5,
   wherein the processing unit moves a support position of the X-ray detector with respect to the rotary unit in the rotational radial direction of the rotary unit and in a tangential direction of a rotation track of the rotary unit to set a position of the X-ray detector.

8. The X-ray CT device according to claim 1, further comprising:
   a treatment table on which the object to be imaged is to be placed.

9. The X-ray CT device according to claim 8,
   wherein the X-ray source and the X-ray detector are disposed in the rotary unit at positions opposite to each other with the treatment table interposed therebetween, and
   the treatment table is supported by a support device fixed to a floor of a building.

10. The X-ray CT device according to claim 1,
    wherein the X-ray detector includes an X-ray detection surface that is perpendicular to a virtual straight line passing through the X-ray source and the reference position, and
    the X-ray detector is capable of switching a state to a first state in which the virtual straight line passes through a center position of the X-ray detection surface, and a second state in which the X-ray detection surface is displaced from the first state in a tangential direction of a rotation track and the virtual straight line passes through an end portion of the X-ray detection surface.

11. The X-ray CT device according to claim 10,
wherein the first state is selected in a case where a size of the object to be imaged is smaller than a predetermined size, and
the second state is selected in a case where the size of the object to be imaged is larger than the predetermined size.

12. The X-ray CT device according to claim 1,
wherein the X-ray detector is movable toward the reference position.

13. The X-ray CT device according to claim 1,
wherein the X-ray source is movable toward the reference position.

* * * * *